United States Patent [19]
Hellmuth et al.

[11] Patent Number: 5,491,524
[45] Date of Patent: Feb. 13, 1996

[54] OPTICAL COHERENCE TOMOGRAPHY CORNEAL MAPPING APPARATUS

[75] Inventors: Thomas Hellmuth, Danville; Jay Wei, Fremont, both of Calif.

[73] Assignee: Carl Zeiss, Inc., Thornwood, N.Y.

[21] Appl. No.: 318,141

[22] Filed: Oct. 5, 1994

[51] Int. Cl.$^6$ .................................................. A61B 3/10
[52] U.S. Cl. .......................... 351/212; 351/221; 351/205
[58] Field of Search ................................. 351/211, 212, 351/205, 221

[56] References Cited

FOREIGN PATENT DOCUMENTS 9219930 11/1992 WIPO .................................. 351/212

OTHER PUBLICATIONS

New Equipment and Methods for Determining the Contour of the Human Cornea by M. G. Townsley, Contacto, 11(4), 1967, pp. 72–81.
Accuracy and Precision of Heratometry, Photokeratoscopy, and Corneal Mapping on Calibrated Steel Balls by S. B. Hannush et al., Arch. Ophthalmol. vol. 107, Aug. 1989, pp. 1235–1289.
Intraoperative raster photogrammetry—the PAR Corneal Topography System by U. W. Berlin, J. Cataract Refract Surg. vol. 19, Suppl, 1993, pp. 188–192.
Micron—Resolution Imaging of the Anterior Eye in Vivo with Optical Coherence Tomography by J. [001e]. Izatt et al., 1994, pp. 1–24.
Optical Coherence Tomography by D. Huang et al., Science, vol. 254 22 Nov., 1991 pp. 1178–1181.
Optical Coherence–domain reflectometry: a new optical evaluation technique by R. C. Youngquist et al., Optics Letters, vol. 12, No. 3, Mar. 1987, pp. 158–160.
Measurement of Corneal thickness by low–coherence interferometry, C. K. Hitzeinberger, Applied Optics, vol. 31, No. 31, Nov. 1, 1992 pp. 6637–6642.
Measurement of the axial eye length and retinal thickness by laser Doppler interferometry (LOI), C. K. Hitzeinberger et al., SPIE vol. 1423 Ophthal Tech. 1991 pp. 46–50.
Micron—Resolution Ranging of Cornea Anterior Chamber of Optical Reflectometry, D. Huang et al. Lasers in Surgery and Medicine, 11, 1991 pp. 419–425.

*Primary Examiner*—William L. Sikes
*Assistant Examiner*—James A. Dudek
*Attorney, Agent, or Firm*—Michael B. Einschlag

[57] ABSTRACT

Optical coherence tomography ("OCT") corneal mapping apparatus includes an OCT apparatus having a rotating helical mirror for altering a reference beam path in the OCT apparatus; a raster scanner for raster scanning sampling optical output from the OCT apparatus; a curved mirror for transferring the sampling optical output from the raster scanner to an eye and for transferring sampling optical output reflected from the eye back to the OCT apparatus through the raster scanner; and an analyzer, coupled to the raster scanner, the rotating helical mirror, and reference and sampling interaction output from the OCT apparatus. The analyzer causes the raster scanner to scan the sampling optical output to points in a raster; causes the rotating mirror to alter the length of the reference beam path over a predetermined amount at each of the points in the raster; and provides the corneal mapping from the reference and sampling interaction output at the points in the raster.

24 Claims, 3 Drawing Sheets

OPTICAL COHERENCE TOMOGRAPHY CORNEAL MAPPING APPARATUS

TECHNICAL FIELD OF THE INVENTION

The present invention relates to a cornea mapping apparatus and, in particular, to an optical coherence tomography corneal mapping apparatus.

BACKGROUND OF THE INVENTION

As is well known, refractive surgery is a surgical procedure that has, as its primary objective, correction of an ametropia by making incisions in a cornea to change the refractive power of the cornea. Surgical manipulation of corneal shape requires an accurate and precise method of measuring anterior corneal curvature from apex to limbus. At present, measurement of curvature of the center of the cornea is commonly made using a keratometer and, for more precise measurements of corneal topography, it is common to utilize photokeratoscopy or videokeratoscopy.

Current corneal topography measurement apparatus are mostly Placido-disc-based videokeratoscopes. In such an apparatus, a series of concentric rings are configured on a cone-shaped housing so that an image reflected from the cornea is virtually flat in space. Then, the configuration of the rings is analyzed to determine the corneal topography. A prior art apparatus of this type has been described in an article entitled "New Equipment and Methods for Determining The Contour of the Human Cornea" by M. G. Townsley, *Contacto*, 11(4), 1967, pp. 72–81. Such videokeratoscopes have the following disadvantages: (a) due to the small radius of the cornea (~8 mm), a limited number of rings can be resolved on the cornea (normally, the contour which can be measured is restricted to an area which ranges from 0.8 to 11 mm in diameter on the cornea); (b) no information can be obtained between the rings; and (c) due to use of rings, in-line measurement is very difficult when used in conjunction with an ophthalmologic surgical microscope. An article entitled "Accuracy and Precision of Keratometry, Photokeratoscopy, and Corneal Modeling on Calibrated Steel; Balls" by S. B. Hannush, S. L. Crawford, G. O. Waring III, M. C. Gemmill, M. J. Lynn, and A. Nizam in *Arch. Ophthalmol*, Vol. 107, August 1989, pp. 1235–1239 provides a comparison of these prior art methods and apparatus.

Another corneal topography measurement apparatus has been developed recently by PAR Microsystem Co. The apparatus utilizes raster photogrammetry to measure a corneal topography. In this apparatus, a grid pattern is projected onto the cornea. The grid pattern is then viewed and imaged from an offset angle. Finally, corneal elevation at each of the discrete points in the grid pattern are calculated using the image of the projected grid pattern, and information relating to its geometry. This apparatus is described in an article entitled "Intraoperative raster photogrammetry—the PAR Corneal Topography System" by M. W. Berlin, *J. Cataract Refract Surg*, Vol. 19, Supplement, 1993, pp. 188–192. Corneal topography measurements suffer in this apparatus because only a limited number of points in the image of the projected grid pattern can be resolved by the image optics.

As is further known, since a posterior corneal surface contributes about −14% of total corneal refractive power, in some cases, an anterior corneal topography, by itself, does not provide sufficient information for use in a refractive surgical procedure. For that reason, it becomes even more important to obtain corneal topography measurements with a precision that cannot be provided by current corneal topography measurement apparatus.

Recently, a new ophthalmic measurement apparatus, an optical coherence tomography ("OCT") apparatus, has been disclosed which has advantages over the above-described prior art ophthalmic measurement apparatus. An OCT apparatus uses a short coherence light source for range measurements based on the principle of white light interferometry. OCT has been proposed recently for use in several ophthalmologic applications. For example, such proposals have been made in a preprint of an article which has been submitted for publication entitled "Micron-Resolution Imaging of the Anterior Eye in Vivo with Optical Coherence Tomography" by J. A. Izatt, M. R. Hee, E. A. Swanson, C. P. Lin, D. Huang, J. S. Schuman, C. A. Puliafito, and J. G. Fujimoto, 1994, pp. 1–24 ("Izatt et al. reference"). The preprint discloses an OCT apparatus which utilizes optical fiber technology and a superluminescent laser diode source, which OCT apparatus is interfaced with a slitlamp biomicroscope for imaging intraocular structures with a spatial resolution of 10–20 µm. The preprint discloses the use of the OCT apparatus to provide direct, micron-resolution measurements of (a) ocular profile dimensions, optical scattering, and structure in the cornea; (b) the anterior angle region; (c) the iris; and (d) the crystalline lens. The preprint further discloses the use of the OCT apparatus to measure: (a) anterior chamber depth, defined as a distance, along the visual axis, from the posterior corneal surface to the lens anterior capsule; (b) radius of curvature of the posterior and anterior surfaces of the cornea; (c) corneal refractive power; and (d) corneal dimensions such as thickness. The preprint still further discloses that the OCT apparatus, using an inexpensive diode laser source and a fiber optic implementation, is compatible with existing ophthalmic instrumentation. Finally, the preprint makes the following suggestions for potential clinical applications of OCT: (a) providing cross-sectional images of the entire anterior chamber for use in elucidating pathologies of the cornea, anterior angle region, and iris and for use in identifying and monitoring intraocular masses or tumors; (b) measuring anterior chamber depth, corneal curvature, and corneal refractive power; and (c) providing high resolution images showing corneal thickness variations and the distribution of scattering in corneal stroma for quantitative analysis of corneal pathologies.

There are two major disadvantages of the above-described OCT apparatus. The first major disadvantage of the above-described device is that the described data acquisition time of several seconds is too long for in vivo measurements of the cornea because saccadic movement of the eye would disturb in vivo measurements. In fact, in practice, in order to preclude disturbance by saccadic movement, data acquisition times smaller than 0.1 seconds are required.

The second major disadvantage of the above-described device is that the signal-to-noise ratio of an OCT signal is determined by shot noise of back scattered light, which shot noise depends on the average number of detected photons. The number of detected photons can be increased by using a brighter OCT beam or by utilizing a longer integration time per sampling point. Either of these methods are problematic. For example, the maximum permissible power of the OCT beam at the cornea of the human eye is limited and regulated by ANSI standards. Second, utilizing a longer integration time per sampling point implies a longer acquisition time for a given number of sampling points and exacerbates the data acquisition problem discussed above.

In light of the above, there is a need in the art for a corneal mapping apparatus which solves the above-identified problens and provides rapid data acquisition and low noise for reconstructing a three-dimensional structure of a cornea.

SUMMARY OF THE INVENTION

An embodiment of the present invention comprises an optical coherence tomography ("OCT") corneal mapping apparatus which solves the above-identified problems in the art by providing rapid data acquisition and low noise for reconstructing a three-dimensional structure of a cornea. In particular, an embodiment of a first aspect of the present invention is an OCT corneal mapping apparatus which comprises: (a) an OCT apparatus which is comprised of means for altering a reference beam path; (b) raster scanning means for raster scanning sampling optical output from the OCT apparatus; (c) curved mirror means for transferring the sampling optical output from the raster scanning means to an eye and for transferring the sampling optical output reflected from the eye back to the OCT apparatus through the raster scanning means; and (d) analyzing means, coupled to the raster scanning means, the altering means, and reference and sampling interaction output from the OCT apparatus for causing: (i) the raster scanning means to move the sampling optical output to points in a raster; (ii) the altering means to alter the length of the reference beam path over a predetermined amount at each of the points; and (iii) determination of the corneal mapping from the reference and sampling interaction output at the points in the raster.

An embodiment of a second aspect of the present invention is an OCT corneal mapping apparatus which comprises: (a) an OCT apparatus which is comprised of means for altering the length of a reference beam path; (b) raster scanning means for raster scanning sampling optical output from the OCT apparatus over an eye and for transferring the sampling optical output reflected from the eye back to the OCT apparatus; and (c) analyzing means, coupled to the raster scanning means, the altering means, and reference and sampling interaction output from the OCT apparatus for causing: (i) the raster scanning means to move the sampling optical output to points in a raster; (ii) the altering means to alter the length of the reference beam path over a predetermined amount at each of the points; (iii) the altering means to alter the length of the reference beam path in response to reference and sampling interaction output obtained at one or more points; and (iv) determination of the corneal mapping from the reference and sampling interaction output at the points in the raster.

BRIEF DESCRIPTION OF THE FIGURE

Components which are the same in the various figures have been designated by the same numerals for ease of understanding.

DETAILED DESCRIPTION

In accordance with the present invention, the data acquisition time of an inventive corneal mapping apparatus is reduced by reducing the sampled volume so that the volume of the cornea which is scanned is small compared to other parts of the anterior chamber of the eye which do not belong to the cornea.

Figure 1:
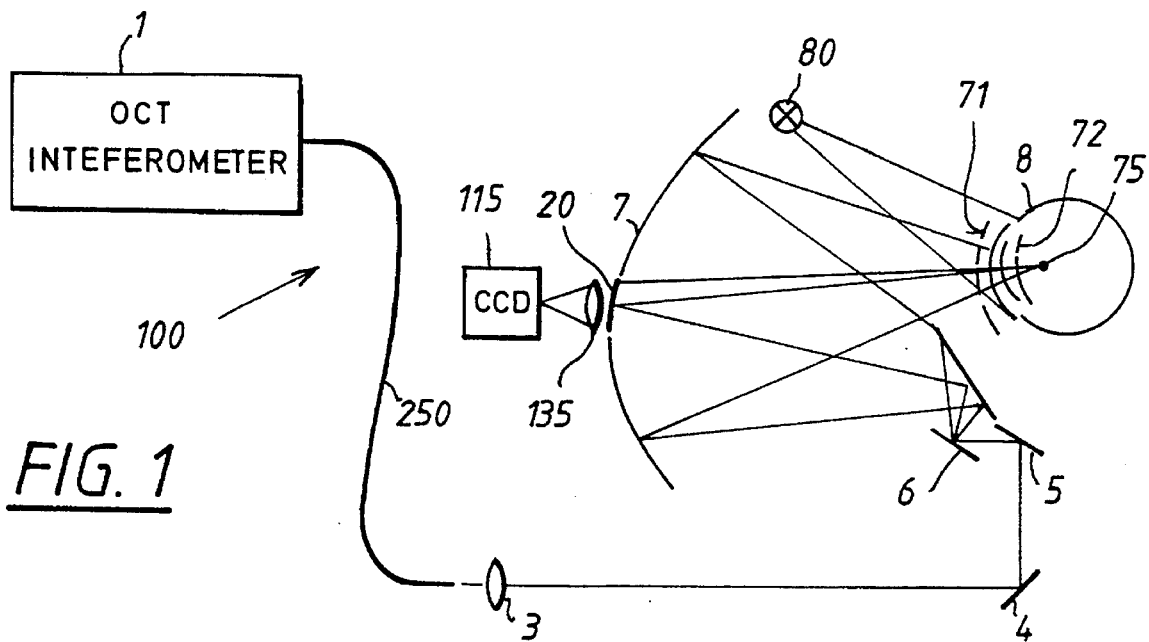
FIG. 1 shows, in pictorial form, a first embodiment of the present invention which comprises an optical coherence tomography ("OCT") corneal mapping apparatus.

FIG. 1 shows, in pictorial form, a first embodiment of the present invention which comprises optical coherence tomography ("OCT") corneal mapping apparatus 100. As shown in FIG. 1, OCT corneal mapping apparatus 100 comprises OCT interferometer 1. An OCT sample beam is output from OCT interferometer 1 in single mode fiber 250. The OCT sample beam output from single mode fiber 250 is collimated by collimator lens 3 and is deflected by mirror 4 to impinge upon scanner mirror 5. The OCT sample beam is then reflected by scanner mirror 5 toward scanner mirror 6 and is reflected, in turn, by scanner mirror 6 toward curved mirror 7. The OCT sample beam is then reflected by curved mirror 7 onto eye 8.

Figure 2:
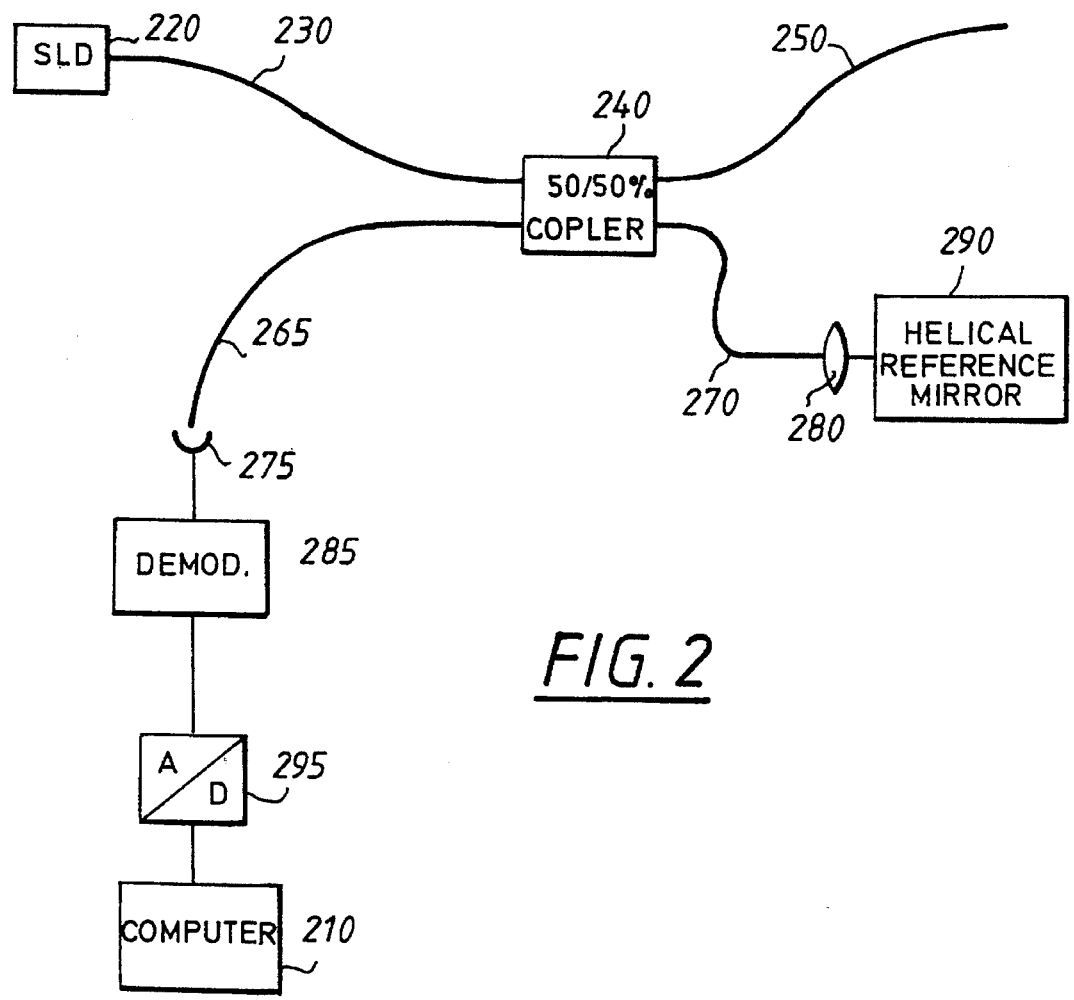
FIG. 2 shows, in pictorial form, a fiber optic embodiment of an OCT apparatus utilized to fabricate the first embodiment shown in FIG. 1.
Figure 3:
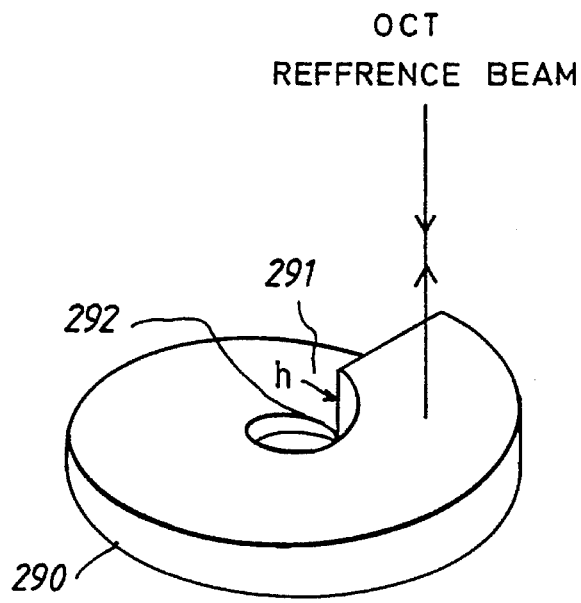
FIG. 3 shows, in pictorial form, a helical mirror utilized to fabricate the OCT apparatus shown in FIG. 1.
Figure 4:
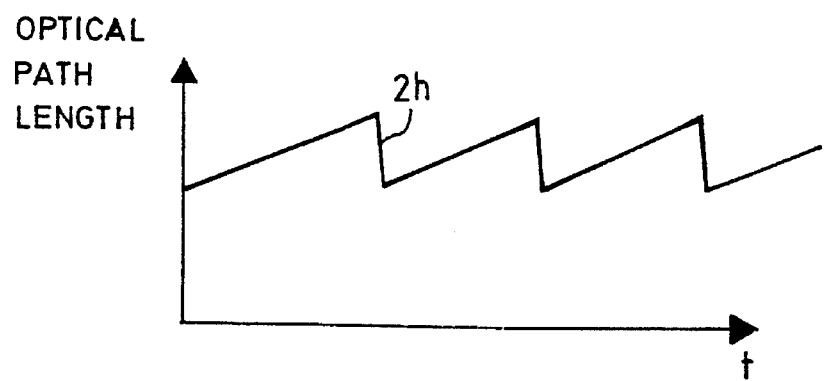
FIG. 4 shows, in graphical form, optical path length as a function of time provided by the helical mirror shown in FIG. 3.

FIG. 2 shows, in pictorial form, a fiber optic embodiment of OCT interferometer 1. As shown in FIG. 2, OCT interferometer 1 comprises CW radiation source 220, for example, a superluminescent laser diode having an output centered substantially at 850 nm. Output from radiation source 220 is coupled into optical fiber 230 and is separated into two beams by 50/50 coupler 240. The output from 50/50 coupler 240 is coupled into optical fibers 250 and 270, respectively. The output from fiber 270 is imaged by lens 280 onto helical reference mirror 290 and the output from fiber 250 is directed to impinge upon eye 8 as was described above. Then, radiation reflected from eye 8 is coupled back into fiber 250 and superimposed by 50/50 coupler 240 with radiation reflected from helical reference mirror 290 and coupled back into fiber 270. Superimposed radiation output from 50/50 coupler 240 is coupled into fiber 265. As is known, there is interference between radiation reflected from the object (eye 8) and radiation reflected from helical reference mirror 290 if the optical path difference is smaller than the coherence length of radiation source 220. As shown in FIG. 3, helical reference mirror 290 is rotated with a substantially constant velocity by means which are well known to those of ordinary skill in the art (not shown) and, as a result, the interference is detected as a periodic variation of a detector signal produced by photodetector 275, the periodic variation having a frequency equal to the frequency of rotation of helical reference mirror 290. The helical surface of helical reference mirror 290 is described by the formula:

$$z = h\phi/2\Pi$$

where h is the step height of the helical surface and $\phi$ is the azimuthal rotating angle. As is known, the reference arm length of OCT interferometer 1 is changed periodically when helical reference mirror 290 is rotated. FIG. 4 shows, in graphical form, the optical path length variation as a function of time produced by rotating helical reference mirror 290. In accordance with the present invention, the height h of the helical surface is chosen so that the depth scan provided by the optical path length variation of the reference arm of OCT interferometer 1 is in the order of the thickness of the cornea. This reduces the scan volume and, thereby, reduces the data acquisition time required for a corneal mapping. In accordance with the present invention, the use of a helical reference mirror is advantageous because it can be rotated very fast and, thereby, a short data acquisition time can be achieved.

As shown in FIG. 2: (a) the output from photodetector 275 is applied as input to demodulator 285 to be demodulated; (b) the demodulated output from demodulator 285 is applied as input to analog-to-digital converter 295 (A/D 295) to be convened to a digital signal; and (c) the digital signal output from A/D 295 is applied as input to computer 210 for analysis. In accordance with the present invention, the interference signal output from photodetector 275 vanishes as soon as the optical path difference between radiation reflected from the object (eye 8) and radiation reflected from helical reference mirror 290 becomes larger than the coherence length of source 220.

Referring back to FIG. 1, to provide transverse scanning of the OCT beam, scanner mirrors 5 and 6 are orthogonally mounted, scanner mirrors which are mounted on a pair of galvanometers (not shown) for scanning. The pair of scanning galvanometers and a motor which rotates helical reference mirror 290 are operated under the control of computer 210 in a manner which is well known to those of ordinary skill in the art. This provides information to computer 210 which enables it to determine three-dimensional coordinates from the geometry of the apparatus; scanner mirrors 5 and 6 providing a raster scan and helical reference mirror 290 providing a depth scan.

In accordance with the present invention, and as shown in FIG. 1, the radius of mirror 7 is chosen so that the principal ray of the scanned beam always goes through the center of curvature 15 of the cornea of eye 8. As the OCT sample beam output from fiber 250 is tranversely scanned by scanner mirrors 5 and 6, the optical path length from 50/50 coupler 240 to dotted curve 71 in front of eye 8 is constant for all positions of scanner mirror 6. Further, this constant optical path length is equal to the optical distance between 50/50 coupler 240 and helical reference mirror 290 for home position 291, i.e., the high point of helical reference mirror 290. In addition, dotted curve 72 describes a curve of equal optical path length for home position 292, i.e., the low point of helical mirror 290. At each transverse position provided by scanner mirrors 5 and 6, helical reference mirror 290 is caused to rotate by 360 degrees to provide a depth scan over a distance of 2h, i.e., the distance between dotted curves 71 and 72. During a depth scan, the OCT signal received by computer 210 provides data which is used to locate the structure of the cornea at the respective transverse position. As one can readily appreciate from this, in accordance with the present invention, the data acquisition time has been shortened by use of a helical mirror and by reducing the depth scan to a distance equal to 2h. In accordance with the present invention, 2h is adjusted to be the minimum distance required to span the corneal thickness.

Figure 6:
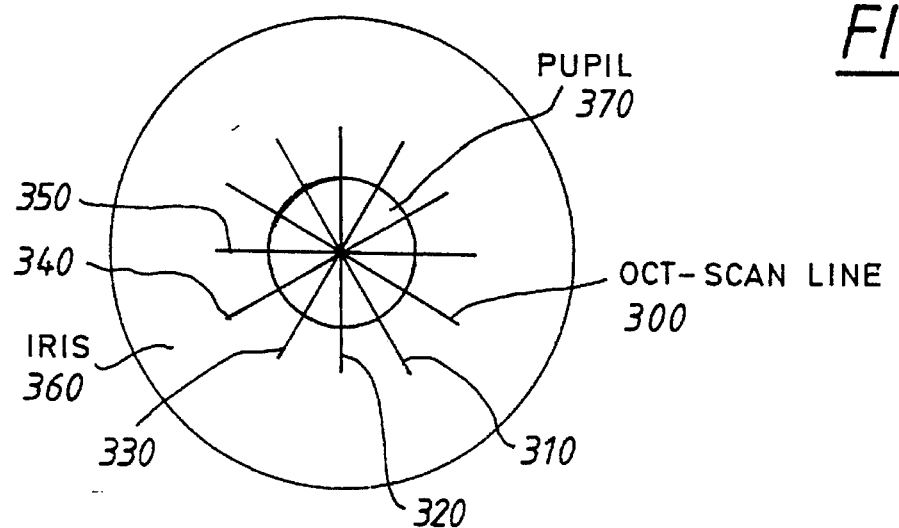
FIG. 6 shows, in pictorial form, a corneal mapping OCT scan pattern.

In accordance with the present invention, eye 8 is monitored using CCD camera 115 which is placed at a position which is conjugate to the iris of eye 8. As shown in FIG. 1, infrared light from infrared source 80 illuminates eye 8. Infrared source 80 is obtained, for example, by filtering an incandescent lamp with an infrared filter. The infrared light illuminated iris of eye 8 is imaged onto CCD 115 by lens 135 through notch filter 20 in curved mirror 7. In accordance with the present invention, notch filter 20 reflects radiation at wavelengths of the OCT sample beam, for example, wavelengths substantially equal to 850 nm, with a reflectivity of about 90% (transmissivity of about 10%) and transmits the infrared light which illuminates eye 8. The reflectivity of the remainder of curved mirror 7 to radiation at wavelengths of the OCT sample beam is also about 90%. The image produced by CCD camera 115 shows eye 8 and a scan trace of the OCT sample beam on the iris and on the vertex of the cornea. The image of the scan trace of the OCT sample beam results from radiation reflected by eye 8 which is transmitted through notch filter 20. A scan trace can be imaged even though transmission of the reflected OCT sample beam is small since CCD camera 115 is very sensitive to radiation at wavelengths in the region of 850 nm. FIG. 6 shows, in pictorial form, a scan pattern produced by OCT corneal mapping apparatus 100. FIG. 6 shows OCT sample beam scan traces 300–350, iris 360, and pupil 370. Because reflection from pupil 370 is very low, the CCD image shows pupil 370 to be dark and to be surrounded by a bright iris 360. Further, the image of OCT sample beam scan traces 300–350 exhibit a dark portion where the scan traces pass though an area corresponding to pupil 370 (except for the vertex of the cornea) and a bright portion when they pass through an area corresponding to iris 360. As a result, one can manually reposition apparatus 100 so that the OCT sample beam scan traces pass through the center of pupil 370. In addition, the image produced by CCD camera 115 can be analyzed by computer 210 to determine the center of pupil 370 by edge detection and the position of the scan traces be adjusted in response thereto.

In response to data acquired during the depth scans, computer 210 identifies various portions of the cornea at a transverse scan point by detecting various signal-strength maxima. In accordance with the present invention, scanner mirrors 5 and 6, in accordance with instructions from computer 210, provide a raster, i.e., transverse, OCT scan of the cornea and OCT interferometer 1, in accordance with instructions from computer 210 to helical reference mirror 290, provides a depth OCT scan of the cornea. The results are analyzed by computer unit 210 to obtain corneal topography measurements such as: (a) anterior corneal surface contours, (b) posterior corneal surface contours, and (c) the thickness of the cornea. These data can be used, for example, for on-line monitoring of corneal refractive power during a refractive surgical procedure or for fitting contact lens and so forth. In one embodiment of this first aspect of the present invention, thresholds are input to computer 210 for the purpose of identifying signal maxima corresponding to predetermined surfaces of the cornea. Then, computer 210 makes a correspondence between signals having levels above the maxima with the predetermined surfaces and captures the spatial coordinates of the surfaces in space from the position of the OCT sample beam in the raster scan and the depth coordinates of the surfaces from the position of helical reference mirror 290 in the depth scan. These values in space are stored in computer 210. The thickness of the cornea can be determined from the spatial difference between signal peaks produced by the posterior and anterior corneal surface during a depth scan and the well known optical properties of the cornea, such as, for example, index of refraction. When the raster scan is completed, computer 210 performs a fit of the spatial coordinates of the surfaces to provide posterior and anterior corneal surface contours. Then, the surface contours are utilized to provide a measure of the curvature of the posterior and anterior surfaces of the cornea and, from them, a measure of corneal refractive power.

Figure 5:
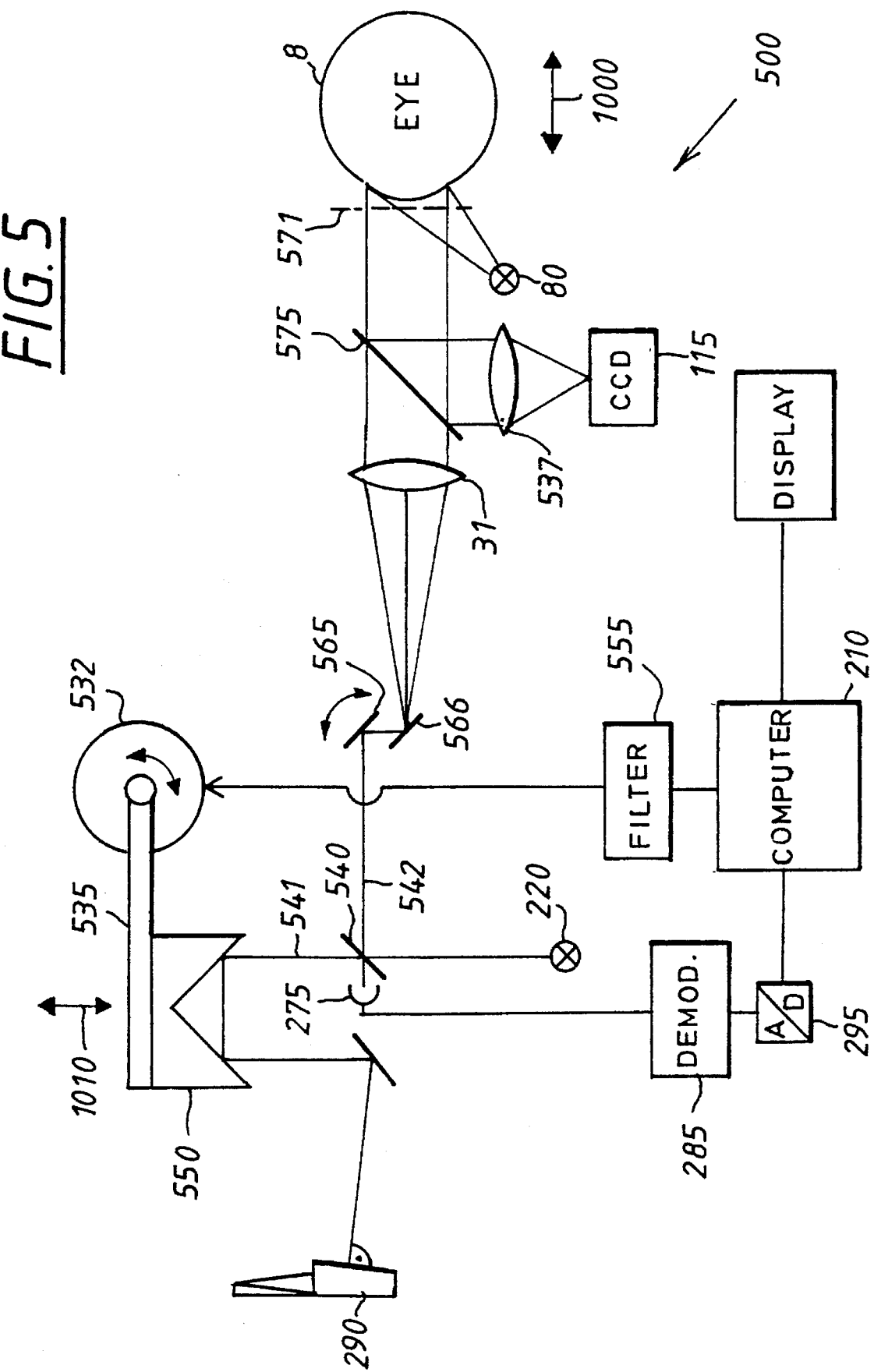
FIG. 5 shows, in pictorial form, a second embodiment of the present invention which comprises an OCT corneal mapping apparatus.

FIG. 5 shows, in pictorial form, a second embodiment of the present invention which comprises OCT corneal mapping apparatus 500. As shown in FIG. 5, OCT corneal mapping apparatus 500 comprises CW radiation source 220, for example, a superluminescent laser diode having an output centered substantially at 850 nm. Output from radiation source 220 is directed toward beamsplitter 540. Beamsplitter 540 splits the output into reference beam 541 which is directed toward retroreflector 550 and sample beam 542 which is directed toward a scanner apparatus, which scanner apparatus is comprised of orthogonally mounted, galvanometer driven scanner mirrors 565 and 566 which are mounted on a pair of galvanometers (not shown). Scanner motors 565 and 566 are operated under the control of computer 210 in a manner which is well known to those of ordinary skill in the art. The raster scanner formed of scanner mirrors 565 and 566 is located in the back focal plane of scanner lens 31. This provides a telecentric optical configuration wherein the principal rays of scanned sample beam 542, in the various scan positions, are parallel. Further, this telecentric optical configuration guarantees that the scan length on the cornea is independent of the cornea in the z direction, i.e., along the direction shown by arrow 1000 in FIG. 5. However, the "surface of equal path length" for a raster scan is a plane which is indicated by dotted curve 571 in FIG. 5. This is disadvantageous in that plane 571 is not adapted to the geometry of the cornea and results in scan volumes and data acquisition times which are larger than are required to determine a corneal mapping. In accordance with the present invention, the scan volumes are decreased by changing the path length of reference beam 541 at various positions of the raster scan. This is done by moving retroreflector 550 to change the path length of reference beam 541 as a function of scan angle of OCT sample beam 542. As shown in FIG. 5, retroreflector 550 is moved by galvanoscanner 532. For example, wand 535 is affixed to galvanoscanner 532 and to retroreflector 550. Whenever galvanoscanner 532 is activated (in a manner which will be described below), wand 535 is rotated and retroreflector 550 is moved along a direction indicated by arrow 1010. Since the required movement of galvanoscanner 532 is small, subsequent movement of retroreflector 550 is substantially along a straight line. As a result, and in accordance with a preferred embodiment of the second aspect of the present invention, the motion of galvanoscanner 532 changes the plane indicated by dotted curve 571 into a spherical surface having a radius substantially equal to the radius of the cornea, which radius is in the order of 8 mm.

As further shown in FIG. 5, reference beam 541 is directed from retroreflector 550 toward helical reference mirror 290. At each transverse position provided by scanner mirrors 565 and 566, helical mirror 290 is rotated by 360 degrees to provide a depth scan over a distance of 2h in the manner discussed above with respect to embodiment 100 shown in FIG. 1. Helical reference mirror 290 is rotated with a substantially constant velocity by means which are well known to those of ordinary skill in the art (not shown). Reference beam 541 is reflected from helical reference mirror 290 and is superimposed, by beamsplitter 540, with radiation from sample beam 542 which is reflected by eye 8. The superimposed radiation is detected by photodetector 275. The output from photodetector 275 is demodulated by demodulator 285, the demodulated output from demodulator 285 is converted to a digital signal by analog-to-digital converter 295 (A/D 295), and the output from A/D 295 is applied as input to computer 210 for analysis.

During a transverse scan of sample beam 542 by scanner mirrors 565 and 566, helical mirror 290 rotates a predetermined number of times, for example, n. The pair of scanning galvanometers which drive scanner mirrors 565 and 566 and a motor which rotates helical reference mirror 290 are operated under the control of computer 210 in a manner which is well known to those of ordinary skill in the art. In accordance with a preferred embodiment of the present invention, OCT data are collected synchronously by computer 210 so that, for example, n depth scans provided by n rotations of helical reference mirror 290 occur during one transverse scan. The OCT signals received by computer 210 from detector 275 are preferably analyzed in real time. The coordinates of various corneal structures are determined by analysis of peaks of the OCT signal received by computer 210 in the manner described above with respect to OCT corneal mapping apparatus 100.

As has been described above, a depth scan is made at predetermined points in the raster or transverse scan. During the depth scan at a point in the transverse scan, particular signal peaks locate particular corneal structures and the depths of the particular corneal structures at the point in the transverse scan depends on the path length difference between reference beam 541 and sample beam 542. However, the path length difference changes as a function of scan angle because of the curved shape of the cornea. In accordance with the second aspect of the present invention, during a transverse scan, computer 210 determines the depth of a particular corneal structure at a first point in the transverse scan, for example, the anterior surface of the cornea, by detecting a signal peak. Next, computer 210 compares the depth of the anterior surface at the first point with the depth of the anterior surface at a predecessor point along the transverse scan. The difference in depth of the anterior surface at the two adjacent points along the transverse scan is used to move retroreflector 550 so that it tracks the curved shape of the cornea. This tracking is done by having computer 210 apply the negative of the difference in depth of the anterior surface at the two adjacent points as an input signal to galvanoscanner 532 through filter 555. In response to this signal, galvanoscanner 532 moves retroreflector 550 so that it causes the depth scan to follow the surface of the cornea. As a result, an effect is produced wherein the surface of constant path length difference, i.e., dotted curve 571, adapts automatically to the surface of the cornea under investigation. In this manner, and in accordance with the present invention, the data acquisition time of the depth scan is shortened. Filter 555 is used to avoid oscillation of galvanoscanner 532 and may be fabricated as a PI-controller which is well known to those of ordinary skill in the art.

Lastly, as shown in FIG. 5, eye 8 is monitored with CCD camera 115 in a manner similar to that shown for embodiment 100 of FIG. 1. In particular, eye 8 is illuminated with infrared light from infrared source 80 which is obtained, for example, by filtering an incandescent lamp with an infrared filter. The infrared light reflected from eye 8 is imaged onto CCD 115 by lens 537 through notch filter 575. In accordance with the present invention, notch filter 575 reflects the infrared light which illuminates the eye and transmits wavelengths of the OCT beam, for example, wavelengths substantially equal to 850 nm.

Those skilled in the art will recognize that the foregoing description has been presented for the sake of illustration and description only. As such, it is not intended to be exhaustive or to limit the invention to the precise form disclosed. For example, modifications and variations are possible in light of the above teaching which are considered to be within the spirit of the present invention. Thus, it is to be understood that the claims appended hereto are intended to cover all such modification and variations which fall within the true scope and spirit of the invention.

What is claimed is:

1. An optical coherence tomography (OCT) corneal mapping apparatus which comprises:

an OCT apparatus which is comprised of means for altering a reference beam path;

raster scanning means for raster scanning sampling optical output from the OCT apparatus;

curved mirror means for transferring the sampling optical output from the raster scanning means to an eye and for transferring the sampling optical output reflected from the eye back to the OCT apparatus through the raster scanning means; and analyzing means, coupled to the raster scanning means, the altering means, and reference and sampling interaction output from the OCT apparatus for causing: (a) the raster scanning means to move the sampling optical output to points in a raster; (b) the altering means to alter the length of the reference beam path over a predetermined amount at each of the points; and (c) determination of the corneal mapping from the reference and sampling interaction output at the points in the raster.

2. The optical coherence tomography (OCT) corneal mapping apparatus of claim 1 wherein the altering means comprises helical reference mirror means disposed in the reference beam path.

3. The optical coherence tomography corneal mapping apparatus of claim 2 wherein the raster scanning means comprises orthogonally mounted mirrors.

4. The optical coherence tomography corneal mapping apparatus of claim 2 which further comprises:

means for irradiating the eye with infrared radiation;

means for detecting the infrared radiation; and means, responsive to output from the detecting means for displaying an image of the eye.

5. The optical coherence tomography corneal mapping apparatus of claim 4 wherein the curved mirror means comprises filter means for transmitting the infrared radiation and a portion of the sampling optical output reflected from the eye to the means for detecting the infrared radiation.

6. The optical coherence tomography corneal mapping apparatus of claim 5 which further comprises means for analyzing the image of the eye to determine a center of a pupil.

7. The optical coherence tomography corneal mapping apparatus of claim 2 wherein:

the surface of the curved mirror means transfers the sampling optical output from the raster scanning means to the eye so that a principal ray of the sampling optical output passes substantially through a center of curvature of the cornea at the points in the raster;

the helical reference mirror means is rotated at a substantially constant velocity; and a step height of a helical surface of the helical reference mirror means is chosen so that the predetermined amount is slightly larger than a thickness of the cornea.

8. The optical coherence tomography corneal mapping apparatus of claim 1 wherein the reference and sampling interaction output comprises one or more maxima at the points in the raster and the analysis means further comprises means: (a) for detecting the one or more maxima of the reference and sampling interaction output at the points in the raster; (b) for associating the one or more maxima with one or more surfaces of the cornea; and (c) for providing contour maps of the one or more surfaces.

9. The optical coherence tomography corneal mapping apparatus of claim 8 wherein the analysis means further comprises means for determining a distance between at least two of the one or more surfaces.

10. The optical coherence tomography corneal mapping apparatus of claim 8 wherein:

the analysis means further comprises means for determining a measure of curvature of a posterior and an anterior surface of a cornea and, from them, a measure of corneal refractive power.

11. The optical coherence tomography corneal mapping apparatus of claim 1 wherein the surface of the curved mirror means transfers the sampling optical output from the raster scanning means to the eye so that a principal ray of the sampling optical output passes substantially through a center of curvature of the cornea at the points in the raster.

12. An optical coherence tomography (OCT) corneal mapping apparatus which comprises:

an OCT apparatus which is comprised of means for altering a length of a reference beam path;

raster scanning means for raster scanning sampling optical output from the OCT apparatus and for transferring the sampling optical output reflected from the eye back to the OCT apparatus; and analyzing means, coupled to the raster scanning means, the altering means, and reference and sampling interaction output from the OCT apparatus for causing: (a) the raster scanning means to move the sampling optical output to points in a raster; (b) the altering means to alter the length of the reference beam path over an amount at each of the points to produce a depth scan wherein a surface of substantially constant optical path length for the raster scan adapts to a surface of the cornea in response to reference and sampling interaction output obtained from one or more points in the raster; and (c) determination of the corneal mapping from the reference and sampling interaction output at the points in the raster.

13. The optical coherence tomography (OCT) corneal mapping apparatus of claim 5 wherein the altering means comprises helical reference mirror means disposed in the reference beam path.

14. The optical coherence tomography corneal mapping apparatus of claim 3 wherein the helical reference mirror means is rotated at a substantially constant velocity; and a step height of a helical surface of the helical reference mirror means is chosen so that the amount is slightly larger than a thickness of the cornea.

15. The optical coherence tomography (OCT) corneal mapping apparatus of claim 12 wherein the altering means for tracking the surface of the cornea comprises movable reflecting means disposed in the reference beam path.

16. The optical coherence tomography (OCT) corneal mapping apparatus of claim 15 wherein the movable reflecting means comprises a retroreflector and wherein the altering means further comprises galvanometer means for moving the retroreflector means.

17. The optical coherence tomography corneal mapping apparatus of claim 12 which further comprises:

means for irradiating the eye with infrared radiation;

means for detecting the infrared radiation; and means, responsive to output from the detecting means for displaying an image of the eye.

18. The optical coherence tomography corneal mapping apparatus of claim 17 which further comprises means for transmitting the infrared radiation and a portion of the sampling optical output reflected from the eye to the means for detecting the infrared radiation.

19. The optical coherence tomography corneal mapping apparatus of claim 18 which further comprises means for analyzing the image of the eye to determine a center of a pupil.

20. The optical coherence tomography corneal mapping apparatus of claim 12 wherein the reference and sampling interaction output comprises one or more maxima at the points in the raster and the analysis means further comprises means: (a) for detecting the one or more maxima of the reference and sampling interaction output at the points in the raster; (b) for associating the one or more maxima with one or more surfaces of the cornea; and (c) for providing contour maps of the one or more surfaces.

21. The optical coherence tomography corneal mapping apparatus of claim 20 wherein the analysis means further comprises means for determining a distance between at least two of the one or more surfaces.

22. The optical coherence tomography corneal mapping apparatus of claim 20 wherein:
the analysis means further comprises means for determining a measure of curvature of a posterior and an anterior surface of a cornea and, from them, a measure of corneal refractive power.

23. The optical coherence tomography corneal mapping apparatus of claim 12 wherein the raster scanning means comprises orthogonally mounted mirrors.

24. An optical coherence tomography (OCT) corneal mapping apparatus which comprises:

an OCT apparatus which is comprised of means for altering a length of a reference beam path;

raster scanning means for raster scanning sampling optical output from the OCT apparatus and for transferring the sampling optical output reflected from the eye back to the OCT apparatus; and analyzing means, coupled to the raster scanning means, the altering means, and reference and sampling interaction output from the OCT apparatus for causing: (a) the raster scanning means to move the sampling optical output to points in a raster; (b) the altering means to alter the length of the reference beam path over an amount at each of the points to produce a depth scan as a function of scan angle of the sampling optical output wherein a surface of substantially constant optical path length for the raster scan adapts to a surface of the cornea; and (c) determination of the corneal mapping from the reference and sampling interaction output at the points in the raster.

* * * * *